United States Patent [19]

Gammons

[11] Patent Number: 4,701,168
[45] Date of Patent: Oct. 20, 1987

[54] APPLICATOR WITH FULCRUM FOR BENDING

[75] Inventor: Clifford E. Gammons, Morgantown, N.C.

[73] Assignee: Span America Medical Systems, Inc., Greenville, S.C.

[21] Appl. No.: 856,357

[22] Filed: Apr. 25, 1986

[51] Int. Cl.$^4$ ............................................. A61M 35/00
[52] U.S. Cl. ......................................... 604/310; 604/1
[58] Field of Search ................ 604/289, 306, 310, 1, 604/2, 3; 128/756, 759; 401/134, 135, 196

[56] References Cited

U.S. PATENT DOCUMENTS

| | | | |
|---|---|---|---|
| 3,344,915 | 10/1967 | Rawlings | 206/56 |
| 3,369,267 | 2/1968 | Friedland et al. | 15/104.94 |
| 3,526,353 | 9/1970 | Jaeschke | 229/51 |
| 3,653,502 | 4/1972 | Beaudoin | 206/60.2 |
| 3,759,375 | 9/1973 | Nappi | 206/63.2 R |
| 3,826,259 | 7/1974 | Bailey | 128/269 |
| 3,891,331 | 6/1975 | Avery | 401/132 |
| 4,140,409 | 2/1979 | DeVries | 401/132 |
| 4,148,318 | 4/1979 | Meyer | 128/269 |
| 4,173,978 | 11/1979 | Brown | 128/269 |
| 4,360,020 | 11/1982 | Hitchcock, Jr. et al. | 604/289 |
| 4,430,013 | 2/1984 | Kaufman | 401/132 |
| 4,493,574 | 1/1985 | Redmond et al. | 401/196 |
| 4,519,795 | 5/1985 | Hitchcock, Jr. et al. | 604/310 |

Primary Examiner—C. Fred Rosenbaum
Assistant Examiner—J. L. Kruter
Attorney, Agent, or Firm—Dority & Manning

[57] ABSTRACT

A disposable applicator has a frangible housing which prior to rupture can effectively maintain a sterile field for storage of antiseptic or the like. Preselected fluid matter is impregnated in an absorbent pad received within the frangible housing. During use, the housing is initially ruptured by peeling away a sealing layer from a supporting member so as to expose the absorbent pad. Then, upright members extending from the housing may be squeezed together for purposes of both handling the applicator and for flexing the remaining housing portion so as to push the absorbent pad away from the housing and towards the target surface. The absorbent pad is received within a concavity of the housing, which concavity tends to be flattened out by squeezing together the upright members which extend from the housing. The applicator presents a large surface area of the absorbent pad to the target surface to which the fluid matter is to be applied while also urging the absorbent pad towards the target surface, thereby enabling an efficient application operation. A high degree of control is also retrieved because the fluid matter is retained below the saturation point of the absorbent pad so that there is no drippage from the pad after it is exposed.

19 Claims, 5 Drawing Figures

APPLICATOR WITH FULCRUM FOR BENDING

BACKGROUND OF THE INVENTION

This invention concerns a pre-sealed applicator which may be opened at time of use to expose absorbent material protectively housed therein. More specifically, a disposable applicator is disclosed for applying sterile antiseptic to a preparation site on a patient, such as prior to making an injection or incision at such site.

Modern health care methodology places high emphasis on the need for general sterility, in both the patient environment and for paraphenalia such as instruments, syringes and the like which routinely or otherwise are brought into such environment. Frequently, such concern for a germ-free environment manifests itself in the form of sterile packed and disposable items for one-time use. For example, entire syringes and thermometers may be individually packaged in a sterile, prepared field, and designed to be disposed after a single use. Plastic gloves, paper gowns and shoe covers, thermometer covers and the like are similar examples of everyday items which typically are packaged in a sterile field and adapted to be disposed after a single use.

Of also great and still growing concern in the modern hospital setting is the cost of providing effective patient care. Hence, many disposable items are already made of relatively inexpensive materials such as paper or plastic instead of cloth or other more substantial materials.

Another aspect of cost consciousness suggests individualized packaging of items so that their consumption may be attributed to a particular patient, department, doctor, etc. Such aspect of cost consciousness is not as critically concerned with the low cost of each individual item (which remains an important factor from another view point) as it is concerned with the accountability of individual items. In other words, it is highly desirable from a cost management view point to be able to associate the costs of treatment and care for individual patients with such patients.

Yet another important concern relative the use of sterile, but disposable items is the working effectiveness of the product itself. Inexpensive plastic gloves in place of more expensive rubber gloves would not be desirable, much less tolerated, no matter how low their price, if their use impaired a surgeon's performance. Likewise, an inexpensive disposable syringe would not be acceptable just because of its low cost if it leaked or otherwise poorly performed during its actual use.

Numerous products achieve various balances among the criteria discussed above.

Disposable applicators or swabs are generally known, examples of such prior devices including:

| U.S. PAT. NO. | INVENTOR(S) | ISSUE DATE |
|---|---|---|
| 4,360,020 | Hitchcock, Jr. et al. | November, 1982 |
| 3,369,267 | Friedland et al. | February, 1968 |
| 4,430,013 | Kaufman | February, 1984 |
| 4,140,409 | DeVries | February, 1979 |
| 4,173,978 | Brown | November, 1979 |
| 3,759,375 | Nappi | September, 1973 |

Hitchcock discloses a plurality of flat cardboard strips joined at their edges. Each strip has an impregnated pad mounted and covered on the surface of a central portion of the strip. The cardboard strips may be separated and wing portions thereof (outside the central portions) folded back to form handles. Either the end portions of the handle wings are folded back or alternatively the wings are drawn up and glued together to define a triangle. The handle tips meeting in such triangle arrangement comprise finger grips for manipulation of the applicator. The triangle arrangement is formed from the farthest edges of the central portions and the tips are used as finger grips. The relatively rigid cardboard strip is not flexed so that the pad mounted on its flat lower surface is pushed away from the cardboard strip.

Friedland similarly has wings which fold back to meet at their edges. A pad member is formed within and throughout such wings, which impedes efficient application of fluid from the farther reaches of such folded-back wings through the small rectangular opening to the pad member which is exposed by removal of a strip panel 22. Such small application surface area of the applicator relative the volume of the pad member further deters efficient application of a desired fluid to a given surface.

Kaufman and DeVries both disclose disposable applicators which permit liquids to be squeezed out of a reservoir through a ruptured slit therein by bending the entire reservoir. Notably, an absorbent pad used to apply liquids freed up from the ruptured reservoir is not enclosed or otherwise apparently maintained sterile prior to its use. Hence, proper sterility is not ensured. Furthermore, Kaufman and DeVries both provide relatively small surface areas for actual fluid application, thereby also having reduced efficiency for application operations, as other products discussed above.

Brown and Nappi are representative of some further efforts typical of prior devices of a disposable antiseptic swab, having a frangible reservoir, for applying fluids using a relatively small surface area for application. Hence, the effectiveness of such applicators is considerably less than would be desired in a number of situations. For example, where speed was required to rapidly administer a shot or prepare an incision field, much time could be consumed in removing the Brown and Nappi swabs from their containers, and in subsequently applying their antiseptics over the desired surface (owing to the relatively small contact surface areas of their swab portions).

SUMMARY OF THE INVENTION

The present invention concerns an improved applicator which is intended to provide better performance in each of the above-stated categories of concern, as well as other areas. A number of problems relative applicators are recognized and addressed by this invention.

For example, one drawback of some prior disposable applicators concerns their lack of effectiveness in performing their intended function, i.e., controllably applying a given fluid matter to a desired surface. The present invention discloses an applicator which during use positively urges its absorbent pad impregnated with antiseptic or the like towards a target surface while not causing the fluid to drip from the pad. Such object generally is achieved by transmitting squeezing force applied to gripper elements, to the applicator support structure so as to flex same, which pushes the absorbent pad out from the applicator. The resulting applicator provides superior controlled and efficient application of antiseptic without any drip.

Flow efficiency of fluid matter from the applicator is further enhanced in a different sense by the relatively large surface area of the absorbent pad which may be presented to the target surface. In accordance with broader aspects of this invention, the absorbent material is maintained in a substantially planar orientation, thereby maximizing available surface area thereof relative its volume for transfer of fluid from the absorbent pad onto the target surface.

Another object of the present invention is efficient, convenient, and rapid controlled application of a given fluid matter to a desired or target surface.

Yet another object of this invention is to provide an applicator which may be readily and easily opened for use, yet prior to being opened remain sufficiently sealed so as to effectively maintain a sterile environment within its enclosed portions, for an indeterminate period of time. Such an applicator is well adapted for lengthy shelf life with continuous integrity.

Still another object of this invention is to provide an applicator which increases efficient flow of fluid matter therefrom during its use by providing a positive force which acts to push the absorbent material towards the desired surface.

Another object of the present invention is to provide a disposable applicator adapted in particular for applying sterile antiseptic in a controlled manner to a preparation site on a patient, such as where an injection or an incision is to be made. A further object is provision of a more general applicator which may be used for applying other types of fluid matter such as oils, inks, make-up, shoe polish or the like, which uses do not require initial sterility, but which nonetheless require a seal sufficient to prevent leakage of the fluids prior to their use.

While an apparatus in accordance with the features of the present invention may assume a wide variety of specific forms, an embodiment of an applicator in accordance with one preferred apparatus comprises a frangible housing including both a flexible base supporting member having upper and lower surfaces, and a removable sealing layer carried on the lower surface of the supporting member; absorbent means, supported on the supporting member and between the sealing layer and the supporting member, for carrying fluid matter; fluid matter carried in the absorbent means; and paired actuation means, operatively associated with the housing, for handling the housing and for being compressed, subsequent to rupture of the housing, so as to project the absorbent means away from the housing thereby facilitating application of the fluid matter onto a target surface.

In yet another construction in accordance with the present invention, structure may be provided for a flexible applicator which tends to project an absorbent pad therefrom during use of the applicator, with such structure comprising a first layer having upper and lower surfaces; a second layer adapted to be frangibly sealed with the first layer so as to define a chamber therebetween; an absorbent pad, received within the chamber, for carrying fluid matter; and two rigid members disposed outwardly from the first layer at a given angle, such that squeezing of the two members towards each other subsequent to separation of the two layers causes the first layer to flex outward so as to push the absorbent pad away from the first layer, and thereby urge the absorbent pad towards a target surface.

In accordance with still another aspect of the present invention, a method is disclosed for using an applicator which has a support method with a concavity on one side thereof and paired upright rigid gripper members protruding from another side thereof, a sealing layer in frangibly sealed relationship with the support member on the one side thereof, and absorbent material impregnated with fluid matter disposed within the concavity and inbetween the support member and the sealing layer, wherein the method includes first separating the sealing layer from the support member to thereby expose for use the absorbent material within the concavity, and then contacting the absorbent material with a target surface while squeezing the gripper members towards each other, the force of such squeezing being transmitted through the gripper members to the support member so as to tend to flatten out the concavity thereof, and thereby urge the absorbent material towards the target surface and away from the support member, thereby facilitating application of the fluid matter on the target surface.

These and numerous other features and aspects of the present invention are set forth in greater detail below.

BRIEF DESCRIPTION OF THE DRAWINGS

The present invention may be completely understood by those skilled in the art upon conducting a study of the following detailed enabling description thereof, taken in conjunction with the accompanying figures, in which.

Figure 1:
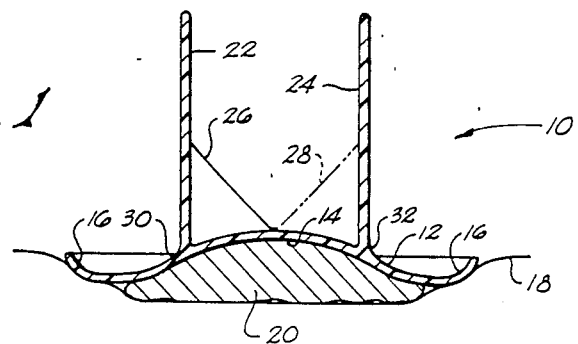
FIGS. 1 and 2 are a side cross-section and top view, respectively, of a first embodiment of the present invention.

Repeat use of reference characters in the following description and on the accompanying figures is intended to represent same or analogous elements or features.

DETAILED DESCRIPTION OF THE PREFERRED EMBODIMENTS

Figure 2:
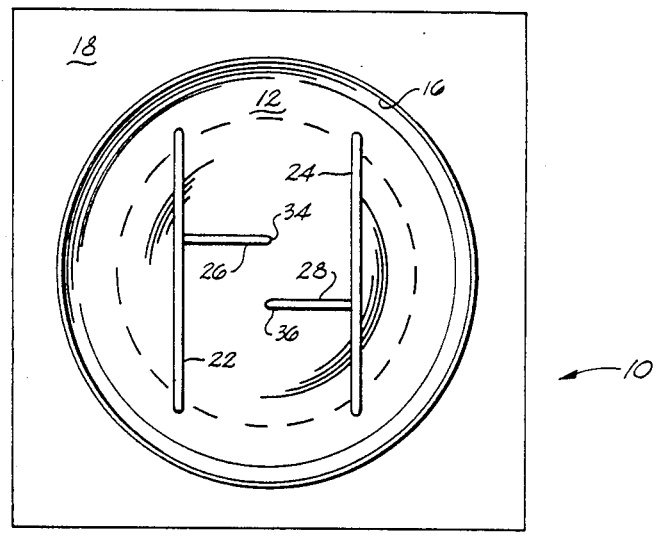

Referring to FIGS. 1 and 2, a first embodiment of an apparatus in accordance with the present invention is illustrated. Applicator 10 has a trangible housing comprised of two generally planar layers 12 and 18. Planar layer 12 may also be viewed as a flexible base supporting member, while layer 18 may be considered to be a removable sealing layer carried on supporting member 12. First layer 12 has a concavity 14 formed on one of its sides, its lower surface. Layer 12 also has a peripheral upturned portion 16, the curvature of which is reverse to that of concavity 14. First layer 12 including all of its features and portions may be integrally formed from any one of a number of different materials, such as injection molded plastics or the like.

Second layer 18 opposes first layer 12. The two layers collectively define a frangible housing. Layer 18 may be comprised of a metallic foil or the like. The second layer may be in frangibly sealed engagement with first layer 12 in the region of upturned portion 16, and/or on the flatter portion of layer 12 located radially between peripheral upturned portion 16 and concavity 14.

As illustrated particularly by FIG. 2, first layer 12 in a preferred arrangement may be formed circular, while second layer 18 is formed as a rectangle. Of course, other shapes for each of layers 12 and 18 come within the scope and teachings of the present invention.

The radial size of layer 12 is related to the size of concavity 14, and hence related to the amount of fluid matter which may be retained for application. Virtually any diameter size for layer 12 is possible. As a practical matter, whenever this invention is adapted to serve as a disposable applicator for preparation of patient sites with sterilized antiseptic, or for a similar function, it is preferred that the diameter of layer 12 come within the range of one to three inches. For example, a diameter of 1⅜ inches permits retention of enough fluid for treatment of a 10 square inch target surface without uncontrolled drippage of any fluid after separation of sealing layer 18 from supporting member 12; a 2 inch diameter device can retain enough fluid to treat a 50 square inch area.

Such physical divisioning of the device and associated amounts of fluid to treat the designated areas permit fluid matter levels to be held below the saturation point for the absorbent pad. Hence, a comfortable and controllable applicator results since there is never any drip or the like from a pad.

In accordance with another aspect of this invention, it is preferred that the outer peripheral portions of second layer 18 extend beyond those of first layer 12 (regardless of its radial dimensions) so that a user may readily grasp sealing layer 18 for separation of same from supporting member 12. A small amount of glue, ultrasonic welding, a pressure sealing, or any of their functional equivalents, may be used to seal the first and second layers 12 and 18 together. Virtually any sort of sealing arrangement or technique may be used so long as it provides the necessary sealing characteristics for a given environment or use, and is readily ruptured by separating (e.g. peeling) sealing layer 18 from supporting member 12.

As stated above, it is not necessary for all uses of this invention that a sterile field be established and maintained in the cavity formed between the first and second layers. It is altogether possible and well within the features of the present invention that a device may be desired (such as one for sealing liquid shoe polish) that requires only a lower grade seal, i.e., one generally sufficient for enclosing the cavity therewithin so as to prevent leaks of the shoe polish, even though not maintaining same in substantially sterile condition.

The specific sealing arrangement used for a particular device and circumstance may also be influenced by the nature of the fluid matter impregnated within an absorbent means 20 enclosed within a cavity formed between layers 12 and 18. Likewise, absorbent means 20 may itself be comprised of a pad of various materials or mixtures thereof, such as non-woven fibers, cotton balls or similar substances, or foam type materials. Selection of a particular type of absorbent material may also take into account the intended use the applicator.

As illustrated in FIG. 1, absorbent means (or absorbent material) 20 is primarily received within concavity 14, which is formed in the lower surface of supporting member 12. It is preferred that absorbent material 20 be at least slightly adhered to the lower surface of supporting member 12 formed by concavity 14 so that such material stays in place during separation of layers 12 and 18, and during subsequent use of applicator 10, as further discussed and illustrated below.

A pair of upright gripper members 22 and 24 comprise actuation means for facilitating both handling of applicator 10, and for being squeezed together so as to flex supporting member 12 outwardly so that concavity 14 tends to flatten out and urge absorbent means 20 towards a target surface. Each of gripper members 22 and 24 are respectively associated with a bracing member or projection 26 and 28 extending between such upright member and supporting member 12.

In a preferred method of using applicator 10, a user grasps upright members 22 and 24 (usually with a thumb and opposing finger of one hand) so as to handle the applicator. Sealing layer 18 is then separated from first layer or supporting member 12 by grasping an exposed peripheral edge of second layer 18 (typically with the thumb and an opposing finger of the user's other hand) and then peeling the two layers apart from each other. Such peeling exposes for use absorbent material 20 impregnated with a desired fluid matter. Absorbent material 20 is held in place with respect to the lower surface of concavity 14, as discussed above. The user then contacts absorbent means 20 with the desired target surface while squeezing upright members 22 and 24 towards one another.

Members 22 and 24 are relatively rigid members which may be formed integrally with layer 12 in an injection molding process. Alternatively, members 22 and 24 may be separately formed and then attached to supporting member 12. Squeezing of members 22 and 24 constitutes a form of actuation which causes members 22 and 24 to tend to pivot at points 30 and 32, respectively. Pivots 30 and 32 are actually the lengthwise hinges formed by the connection of members 22 and 24, respectively, with first layer 12 (see FIG. 2). During squeezing, bracing members or projections 26 and 28 are likewise pivoted about hinges 30 and 32, respectively, thereby causing force to be transmitted from members 22 and 24 therethrough and then in a direction which tends to oppose or flatten out concavity 14.

As is more clearly illustrated by FIG. 2, projection 26 acts to transmit force principally at point 34 while projection 28 acts likewise at point 36 to press outwardly on the backside of concavity 14, thereby tending to flatten out same. Such action serves to press out on (and to some extent, compress) absorbent means 20, thereby urging absorbent means 20 towards a desired target surface. In such manner, which generally conforms with the broader teachings of this invention, fluid matter is efficiently applied to a target surface under the positive urgings achieved with use of actuation means formed by the structure discussed above.

Typically during use, absorbent means 20 is brought into physical contact with the target surface. In such instance, the effect of outward pressure on concavity 14 (and hence absorbent means 20) created by squeezing members 22 and 24 together is further enhanced since absorbent means 20 is trapped on its opposite side by the target surface.

FIG. 1 illustrates projections 26 and 28 as solid triangular members which fill-in the approximate right angles formed, respectively, between upright members 22 and 24 and supporting member 12. Bracing elements 26 and 28 of this invention are not limited to such structure, however, and may comprise other embodiments such as stiffened rod structures or the like extending between support member 22 and point 34, and between support member 24 and point 36. Points 34 and 36 are relatively near the center of concavity 14, and provide the focus for forces transmitted from members 22 and 24 which tend to oppose concavity 14.

Also, members 22 and 24 may be initially disposed at some predetermined angle with respect to surface 12 other than the substantially perpendicular relationship shown in the exemplary embodiment of FIG. 1. In such instances, bracing projections 26 and 28 may be modified as needed so as to extend in an operative manner between supporting member 12 and their respective upright members 22 and 24.

Figure 3:
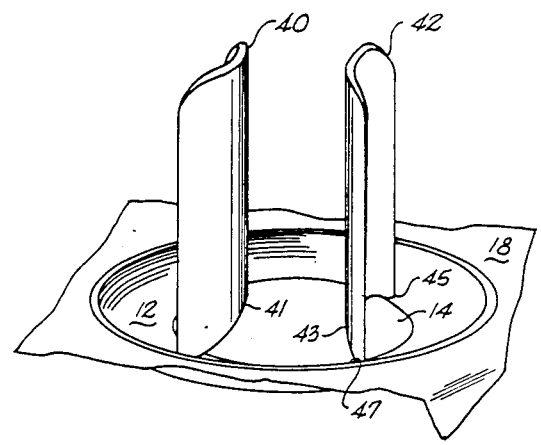
FIG. 3 is a perspective side view of a second embodiment of the present invention.

Referring now to FIG. 3, a second exemplary embodiment of an applicator in accordance with the general teachings of this invention is illustrated. In such construction, upright members 22 and 24 and their respective bracing projections 26 and 28 (shown in FIGS. 1 and 2) are replaced with upright elements 40 and 42. Elements 40 and 42 respectively have radii of curvature which oppose each other, as illustrated. In other words, projections 40 and 42 present convex curvatures to one another. Such structure performs at least two functions. First, the curvature of upright members 40 and 42 enhance the ease with which such members may be gripped by a user since the curvature can be matched for receipt of a user's fingers. Upright members 40 and 42 (as well as 22 and 24 for the other embodiment) may also be provided with roughened surfaces which further enhance such gripability.

As a second function, the curved base of each member 40 and 42 may be integrally formed or attached with supporting member 12 so as to provide three-point action with same in a manner analogous to the combined actions of elements 22-28 of the first embodiment. Those base portions of members 40 and 42 which are closest to each other (approximately at points 41 and 43, centers respectively) perform in a manner analogous to points 34 and 36 (illustrated in FIG. 2) to be the focus of transmited forces from members 40 and 42 as they are squeezed together, which transmitted forces tend to flatten out concavity 14 of first layer 12. Such flattening tends to drive or push out absorbent means 20 from concavity 14 and supporting member 12 in precisely the same manner as discussed above with reference to FIGS. 1 and 2. The three-point action of each member 40 and 42 is defined by their respective center points 41 and 43, and the two end points of each such base. For example, such two end points for the base of member 42 are illustrated at points 45 and 47 in FIG. 3.

Upright members in accordance with the present invention are joined with first layer 12 substantially near the peripheral edges of concavity 14. Such placement provides for maximum pivoting action (and hence leverage) about the base portions of such upright members relative the concavity. Also, FIGS. 1-3 show upright members 22, 24, 40, and 42 as formed substantially perpendicular to supporting member 12. Virtually any predetermined angular relationship with the first layer is sufficient, although the illustrated perpendicular relationship is preferred for ease of manufacture of the applicator, and for handling and use of same since leverage for flattening concavity 14 and pushing outwardly on absorbent pad 20 is thereby efficiently obtained.

Figure 4:
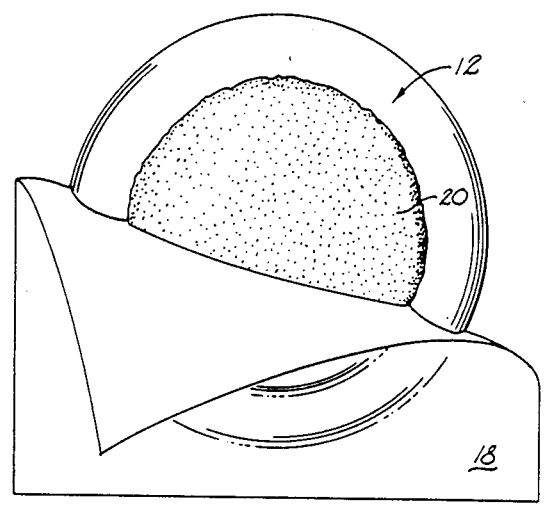
FIG. 4 is a bottom view of an apparatus in accordance with the present invention, with a sealing surface thereof partially removed.

FIG. 4 illustrates a view looking towards the lower surface (i.e., the absorbent material surface) of an applicator constructed in accordance with the general teachings of this invention, with second layer 18 thereof partially separated and peeled away from first layer 12. Such bottom view more fully illustrates the fact that both absorbent means 20 and the bottom surface of first layer 12 are enclosed and protected by sealing layer 18 up until such time as such layer is removed from the base supporting member. Whenever application of sterilized fluid matter is desired, such construction of the lower surface (concavity side) of first layer 12 relative such second layer 18 is of practical significance since such lower surface of layer 12, which may come into contact with a target surface, is also maintained in a sterile condition up until removal of second layer 18.

FIG. 4 also serves to illustrate another feature of this invention, i.e., the fact that more than one-half of the bottom surface area of first layer 12 is covered by absorbent means 20. Hence, that portion of absorbent pad 20 actually contacting the target surface is large relative the volume of such pad 20, which provides for efficient and unimpeded application of given fluid matter to a desired target surface, while dispersing the pressure of such application over an increased surface area. Fluid available for application is also maximized without causing drippage of such fluid, thereby affording superior control of the application process.

Wound or preparation sites are often highly sensitive to touch and pressure. Increased surface area of a device constructed in accordance with this invention permits application of fluid matter to a possible wound site with less pressure thereto and in less time than previously required by smaller pencil-like applicators of prior devices, referenced above. Enhanced patient comfort while dabbing or rubbing on antiseptic or other topical treatments using a construction in accordance with the present invention significantly and uniquely benefits the usefulness and effectiveness of such a product over many typical prior products. Of course, the positive force exerted by the leverage system described above to project absorbent means 20 towards the target surface further facilitates the application process for treating a wound or other treatment field.

Figure 5:
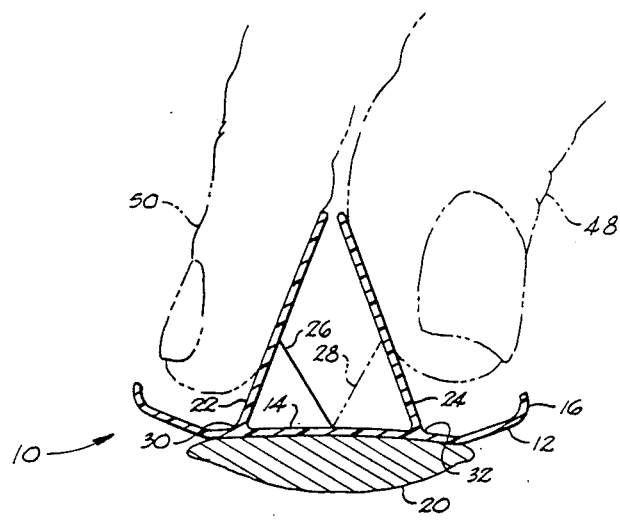
FIG. 5 is a perspective cross-section of an apparatus in accordance with the present invention during use of same.

FIG. 5 illustrates more vividly the operation and function of a construction in accordance with the present invention during use thereof. In FIG. 5, sealing layer 18 has already been separated and removed from first layer 12 so that absorbent means 20 is exposed and ready for use. As illustrated, a user has grasped gripper elements 22 and 24 to facilitate handling of applicator 10. In the pictured exemplary embodiment, a user is performing a preferred method of use of applicator 10 by using the thumb 48 and an opposing finger 50 on one of their hands to engage upright members 22 and 24 and squeeze them together.

As discussed above, upright members 22 and 24 are relatively rigid members which pivot about points 30 and 32 during such squeezing. Support projections 26 and 28 are also respectively pivoted about such points by members 22 and 24, generally inwardly towards the center and back of concentricity 14 formed within surface 12. Force transmitted from members 22 and 24 through support projections 26 and 28 to surface 12 cause concentricity 14 to tend to flatten out, as illustrated in FIG. 5. Such action causes absorbent means 20 to be pushed outwardly from concentricity 14 and consequently urged towards the target surface. Absorbent means 20 will also be compressed so as to release its fluid matter if the absorbent material is trapped against a desired target surface to which fluid matter is being applied. Hence, the fluid matter within absorbent means 20 is more effectively applied to a desired surface.

As a further consequence of the pivoting action of upright members 22 and 24 (illustrated by FIG. 5), and the resultant flattening force applied near the center and back of concentricity 14, the outer peripheral portions of layer 12 which define upturned portions 16 thereof are further pushed away from (i.e., pulled back from) the target surface to which fluid matter is being applied. Such pullback action further minimizes contact of applicator 10 with the target surface, other than the desired contact between absorbent means 20 (with its impregnated fluid matter) and the subject surface to be treated.

Furthermore, the above-noted dynamic pullback action of upturned portion 16 ensures that typically softer material, from which absorbent means 20 will be made, is brought into contact with the target surface instead of harder plastic material, which layer 12 is likely to be composed of. Hence, dynamic action (illustrated for example by FIG. 5) of an applicator constructed in accordance with the teachings of this invention enhances the safety, comfort, effectiveness, and usefulness of such an applicator when used to treat patients. Likewise, in a shoe polish adaptation, the drawback feature could prevent the finish of the shoe from being marred or scratched by contact with the harder supporting member instead of the softer absorbent material.

As mentioned above, numerous modifications and variations to the above-disclosed exemplary embodiments come within the broader aspects of the present invention. Any manner or variety of fluid matters (including those of widely varying viscosities) may be impregnated in absorbent means 20. For example, means 20 may be impregnated with a specified amount of shoe polish to serve as a traveling touch-up kit or the like. Alternatively, make-up or some topical ointment or preparation could be impregnated into absorbent means 20.

Further, the structure of the applicator itself could be modified in any number of ways to adapt to various design criteria. For example, layers 12 and 18 could assume shapes other than the circular and rectangular shapes respectively illustrated. Also, upward projections 22 and 24 may assume various shapes, and be initially disposed at various predetermined angles with respect to layer 12.

Also, it is not essential that layer 12 be provided with upturned outer peripheral portion 16. Layer 12 could be instead formed more planar in its peripheral portions which extend radially outward from concentricity 14. Bracing projections 26 and 28 need not be limited to a single element each, but instead could comprise several elements each, which collectively function to transmit force from their respective upright elements to layer 12. Alternatively, it is possible to omit either one of projections 26 and 28 (as suggested in FIG. 1, which illustrates bracing projection 28 in dotted line) so that a single bracing projection transmits the force used in squeezing elements 22 and 24 together into a flattening force applied to concavity 14.

Any and all such variations and modifications which would occur to one of ordinary skill in the art, and all functional equivalents thereof, are intended to come within the features of the present invention, and hence fall within the scope of the appended claims. The foregoing embodiments are considered to be exemplary and descriptive only, as is the language describing same, words of limitation appearing only in the following claims.

What is claimed is:

1. A medicant applicator, comprising:

a frangible housing, including a flexible base supporting member having upper and lower surfaces; and a removable sealing layer carried on said lower surface of said supporting member;

absorbent means, supported on said supporting member and between said sealing layer and said supporting member, for carrying fluid matter;

fluid matter carried in said absorbent means; and paired curved actuation means, forming a fulcrum at said upper surface of said housing, and relatively rigidly secured to and extending vertically erect from said upper surface of said housing, for handling of said housing and for being selectively laterally compressed so as to project said absorbent means away from said housing by flexing said base outward thereof, thereby facilitating application of said fluid matter onto a target surface subsequent to rupture of said housing.

2. An applicator as in claim 1, wherein said supporting member and sealing layer comprise substantially planar opposing surfaces, with said supporting member being slightly profiled for receipt of said absorbent means therein between said supporting member and said sealing layer.

3. An applicator as in claim 2, wherein:

said housing is initially sealed to an extent sufficient for maintaining a sterile field between said supporting member and said sealing layer; and wherein rupture of said housing is defined by separation of said supporting member and sealing layer from each other, whereby said absorbent means, previously enclosed within said housing, is exposed for use.

4. An applicator as in claim 3, wherein:

said absorbent means is secured to said supporting member so as to not be displaced therefrom by rupture of said housing; and said sealing layer comprises a metallic film carried on said lower surface of said supporting member and adapted to be peeled therefrom.

5. An applicator as in claim 1, wherein said fluid matter comprises an antiseptic such as PVP iodine, and said iodine is impregnated in said absorbent means.

6. An applicator as in claim 2, wherein said actuation means comprise:

a pair of substantially rigid elements disposed during rest at given angles with respect to said housing; and brace members operatively associated with said housing and said pair of rigid elements so that compression of said rigid elements towards each other transmits forces through said brace members acting on said flexible supporting member which tends to flex said supporting member outwardly so as to push said absorbent means away from said supporting member.

7. An applicator as in claim 3, wherein:

at least one half of the area of said lower surface is covered by said absorbent means;

said fluid matter carried in said absorbent means is present in a volume less than the saturation point of said absorbent means to prevent any drippage of said fluid matter from said absorbent means, thereby facilitating efficient and controlled application of said fluid matter to a target surface.

8. A medicant applicator, comprising:

a frangible housing, including a flexible base supporting member having upper and lower surfaces, and a removable sealing layer carried on said lower surface of said supporting member;

absorbent means, supported on said supporting member and between said sealing layer and said supporting member, for carrying fluid matter;

fluid matter carrier in said absorbent means; and paired curved actuation means, secured to said housing, for handling of said housing and for being compressed so as to project said absorbent means away from said housing, thereby facilitating application of said fluid matter onto a target surface subsequent to rupture of said housing; wherein said supporting member and sealing layer comprise substantially planar opposing surfaces, with said supporting member being slightly profiled for receipt of said absorbent means therein between said supporting member and said sealing layer;

said profile of said supporting member is slightly concave and opens towards said lower surface of said supporting member with said absorbent means received therein; and said actuation means functions when compressed so as to press on such concavity in a direction which tends to flatten same, thereby pushing outwardly on said absorbent means received therein to facilitate application of said fluid matter onto a target surface.

9. An applicator as in claim 8, wherein:

said supporting member has an upturned peripheral edge located radially outside said concavity, the curve of which is directed reverse to that of said concavity; and said sealing layer of said housing has a peripheral portion which is matingly associated with said upturned peripheral edge whenever said sealing layer is carried on said supporting member; and wherein compression of said actuation means causes said peripheral edge of said supporting member to drawback in a direction opposite to that which said absorbent means is projected during such compression, thereby minimizing contact of such peripheral edge with a target surface to which said fluid matter is to be applied.

10. A medicant application, comprising:

a frangible housing, including a flexible base supporting member having upper and lower surfaces, and a removable sealing layer carried on said lower surface of said supporting member;

absorbent means, supported on said supporting member and between said sealing layer and said supporting member, for carrying fluid matter;

fluid matter carried in said absorbent means; and paired actuation means, secured to said housing including planar transverse fulcrum means, for handling of said housing and for being compressed so as to project said absorbent means away from said housing, thereby facilitating application of said fluid matter onto a target surface subsequent to rupture of said housing; wherein said supporting member and sealing layer comprise substantially planar opposing surface, with said supporting member being slightly profiled for receipt of said absorbent means therein between said supporting member and said sealing layer; and said actuation means comprise at least two substantially rigid upright members formed integrally with said housing, said members when compressed towards each other pivoting relative said housing so as to generally flatten said profile thereof and thereby push said absorbent means away from said housing.

11. Structure for a flexible medicant applicator which tends to project an absorbent pad therefrom during use, said structure comprising:

a first layer having upper and lower surfaces;

a second layer adapted to be frangibly sealed with said first layer so as to define a chamber therebetween;

an absorbent pad received within said chamber, for carrying fluid matter; and two rigid members disposed outwardly from said first layer at a given angle, and planar transverse fulcrum means respectively interconnecting said rigid members to said first layer, such that squeezing of said two members towards each other causes said first layer to flex outward so as to push said absorbent pad away from said first layer and thereby facilitate urging of said absorbent pad towards a target surface subsequent to separation of said layers; and wherein said first layer is formed slightly concave and receives said absorbent pad in such concavity; and further wherein said squeezing of said two members tends to oppose said concavity of said first layer so that said absorbent pad is pushed away from said first layer, thereby facilitating application onto a target surface of fluid matter carried by said absorbent pad.

12. Structure as in claim 11, further comprising rigid projections extending respectively between each of said members and said first layer so as to form a dual lever arrangement adapted for transmitting force from said rigid members to said first layer, whenever said two rigid members are squeezed towards one another, which force tends to flatten said concavity formed in said first layer so that said absorbent pad is projected from said applicator.

13. Structure as in claim 11, wherein:

said first layer is generally planar, except for said slight concavity thereof which is centrally formed therein and covers at least one half of the surface area of said first layer; and said two rigid members comprise two upright planar elements, facing each other and formed generally perpendicular to and integrally with said first layer near peripheral portions of said concavity on a side of said first layer opposite said concavity, whereby such structure maximizes leverage generated by said two upright elements being squeezed together for flexing said first layer outward and pushing said absorbent pad away from said first layer.

14. Structure as in claim 13, further comprising bracing elements which extend towards the center of saisd concavity between each of said two upright elements, respectively, and said first layer, said bracing elements being pivoted generally about points where said two upright elements integrally attach with said first layer by squeezing of said two elements, and thereby transmiting force from such squeezing to said first layer in a direction tending to oppose said concavity thereof, which transmitted force positively flexes said first layer outwardly so as to push said absorbent pad away therefrom.

15. Structure as in claim 11, wherein:

said two rigid members comprise two upright elements disposed generally at predetermined angles to said first layer, with each of said elements having respective radii of curvature away from one another, curved bases of said two elements being integrally formed with said first layer to permit three-point action by each of said rigid members on said first layer whenever said two rigid members are squeezed towards one another, resulting in application of a central force to said first layer which tends to oppose its concavity, thereby pushing said absorbent pad received therein away from said first layer.

16. Structure as in claim 11, wherein:

said first layer is generally circular and has a diameter in the range of one to three inches;

said second layer is generally rectangular and has a layer surface area larger than that of said first layer, resulting in peripheral portions thereof extending beyond said first layer, which peripheral portions facilitate gripping of said second layer for separation of same from said first layer;

said first layer has a peripheral upturned portion, curved oppositely to said concavity of said first layer; and said second layer is in frangible sealing engagement with said upturned portion of said first layer sufficient to maintain a sterile field within said chamber formed between said first and second layers; and wherein squeezing of said two rigid members, tending to cause said first layer to flex outward and said absorbent pad to be pushed away from said first layer, also causes said peripheral upturned portion of said first layer to be flexed in a direction opposite to that in which said absorbent pad is pushed, thereby permitting fluid matter carried by said absorbent pad to be readily applied to a target surface without said first layer touching said target surface.

17. Structure as in claim 11, wherein:

said second layer comprises metallic foil;

said absorbent pad comprises absorbent material such as one of foam and nonwoven fiber;

said absorbent pad carries fluid matter comprising an antiseptic; and said first layer and said two rigid members integrally comprise a plastic material, with said two rigid members each having a roughened surface for enhanced friction gripping thereof by users of said applicator.

18. A method for using an applicator which has a support member with a concavity on one side thereof and paired upright rigid gripper members protruding from another side thereof, a sealing layer in frangibly sealed relationship with said support member on said one side thereof, and absorbent material impregnated with fluid matter disposed within said concavity and inbetween said support member and sealing layer, said method comprising the steps of:

(a) separating said sealing layer from said support member, thereby exposing for use said absorbent material within said concavity; and (b) contacting said absorbent material with a target surface while squeezing said gripper members towards each other, the force of such squeezing being transmitted through said gripper members to said support member so as to tend to flatten out said concavity and thereby urge said absorbent material towards said target surface and away from said support member, which facilitates application of said fluid matter to said target surface.

19. A method as in claim 18, wherein:

said fluid matter is antiseptic;

said sealed relationship includes sterile packing of said absorbent material within said concavity; and said target surface comprises skin;

whereby use of the method constitutes preparation with a sterilized antiseptic of one of an injection and incision sight on a patient.

* * * * *